United States Patent
Mikkaichi et al.

(10) Patent No.: US 8,002,695 B2
(45) Date of Patent: Aug. 23, 2011

(54) MEDICAL PROCEDURE VIA NATURAL OPENING

(75) Inventors: Takayasu Mikkaichi, Tokyo (JP);
Kensei Nakahashi, Tokyo (JP);
Kunihide Kaji, Tokyo (JP); Hironobu Kawano, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 647 days.

(21) Appl. No.: 11/331,966

(22) Filed: Jan. 13, 2006

(65) Prior Publication Data

US 2007/0173859 A1 Jul. 26, 2007

(51) Int. Cl.
*A61B 1/00* (2006.01)
*A61B 1/12* (2006.01)

(52) U.S. Cl. ........................ 600/104; 600/158

(58) Field of Classification Search .................. 600/104, 600/114, 120, 153, 156, 158, 159, 563, 593, 600/115, 116; 604/101.05, 101.01–101.03, 604/101.04, 102.01
See application file for complete search history.

(56) References Cited

U.S. PATENT DOCUMENTS

| | | | |
|---|---|---|---|
| 4,178,940 A | 12/1979 | Au | |
| 4,180,076 A | 12/1979 | Betancourt | |
| 4,445,892 A * | 5/1984 | Hussein et al. | 604/101.05 |
| 5,167,627 A * | 12/1992 | Clegg et al. | 604/103.03 |
| 5,297,536 A * | 3/1994 | Wilk | 600/104 |
| 5,458,131 A * | 10/1995 | Wilk | 600/105 |
| 5,527,280 A | 6/1996 | Goelz | |
| 6,027,499 A * | 2/2000 | Johnston et al. | 606/22 |
| 6,238,335 B1 * | 5/2001 | Silverman et al. | 600/29 |
| 6,991,602 B2 * | 1/2006 | Nakazawa et al. | 600/101 |
| 2001/0049497 A1 | 12/2001 | Kalloo et al. | |
| 2005/0033331 A1 | 2/2005 | Burnett et al. | |
| 2005/0222491 A1 | 10/2005 | Uesugi et al. | |
| 2005/0234391 A1 | 10/2005 | Noda et al. | |
| 2005/0273060 A1 | 12/2005 | Levy et al. | |
| 2006/0229653 A1 * | 10/2006 | Wilk | 606/185 |
| 2006/0241344 A1 * | 10/2006 | Wilk | 600/114 |
| 2006/0241570 A1 * | 10/2006 | Wilk | 606/1 |
| 2007/0123781 A1 * | 5/2007 | Callahan et al. | 600/483 |

FOREIGN PATENT DOCUMENTS

| | | |
|---|---|---|
| JP | 2002-153563 | 5/2002 |
| JP | 2003-506132 | 2/2003 |
| JP | 2005-287839 | 10/2005 |
| JP | 2005-287840 | 10/2005 |
| WO | WO 01/10314 A2 | 2/2001 |

OTHER PUBLICATIONS

U.S. Office Action dated Apr. 28, 2010, received in related U.S. Appl. No. 11/652,954.
United States Office Action issued Oct. 27, 2010 in corresponding U.S. Appl. No. 11/652,954.

* cited by examiner

*Primary Examiner* — Linda C Dvorak
*Assistant Examiner* — Alireza Nia
(74) *Attorney, Agent, or Firm* — Scully, Scott, Murphy & Presser, P.C.

(57) ABSTRACT

The medical procedure via a natural opening according to the present invention includes: adjusting the patient's body so that a target site on the anterior wall of a hollow organ faces in the direction opposite to the direction of gravitational force; introducing a liquid inflow conduit in the vicinity of the target site, and flowing liquid into the hollow organ via the liquid inflow conduit, to form a liquid holding area and a gas retaining area inside the hollow organ; introducing an observation device into the hollow organ, and confirming the position of the target site from the position of the gas retaining area; and incising while observation the target area.

13 Claims, 9 Drawing Sheets

MEDICAL PROCEDURE VIA NATURAL OPENING

BACKGROUND OF THE INVENTION

1. Field of the Invention

The present invention relates to a medical procedure performed via a natural opening.

2. Description of Related Art

Laparoscopic surgery is a conventionally known technique that has been employed when performing a medical procedure such as observation or treatment of the internal organs of the human body. Rather than making a large abdominal incision, laparoscopic surgery provides's for the procedure to be's-carried out's by making several openings in the abdominal wall, and inserting a laparoscope and surgical instruments such as forceps into these respective openings. This type of surgery offers the benefit of reduced stress on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. One example of such a procedure is disclosed in U.S. Pat. No. 5,458,131.

In this method, a flexible endoscope is inserted via the mouth of the patient. An opening is made in the stomach wall and the end portion of the endoscope is sent out through this opening into the abdominal cavity. Then, while employing the endoscope as an observation device for the inside of the abdominal cavity, the desired medical procedure is performed within the abdominal cavity using instruments inserted through the endoscope or via another opening.

SUMMARY OF THE INVENTION

An object of the present invention is to provide a method that enables easier confirmation of a specific site on a hollow organ, by using an observation device that has been guided into the hollow organ. The present invention further provides a device for this method.

The medical procedure via a natural opening according to a first aspect of the present invention includes: adjusting the patient's body position so that a target site on the anterior wall of the hollow organ faces in the direction opposite to the direction of gravitational force; introducing a liquid inflow conduit in the vicinity of the target site, flowing liquid into the hollow organ via the liquid inflow conduit, to form a liquid holding area and a gas retaining area inside the hollow organ; introducing an observation device into the hollow organ, and confirming the position of the target site from the position of the gas retaining area; and incising while observation the target area.

The medical procedure via a natural opening according to a second aspect of the present invention includes: adjusting the patient's body position so that the target site on the anterior wall of the hollow organ faces in the direction opposite to the direction of gravitational force; introducing a liquid inflow conduit in the vicinity of the target site via a natural opening; flowing a liquid into the hollow organ via the liquid inflow conduit, to form a liquid holding area and a gas retaining area inside the hollow organ; confirming the position of the gas retaining area by using an observation device introduced into the hollow organ via the natural opening, and confirming the target site based on the position of the gas retaining area; and performing a procedure at the target site while observation the target site.

DESCRIPTION OF THE PREFERRED EMBODIMENTS

Embodiments according to the present invention will now be explained in detail below. Structural elements that are equivalent in the following discussion will be assigned the same numeric symbol and redundant explanation thereof will be omitted.

First Embodiment

Figure 1:
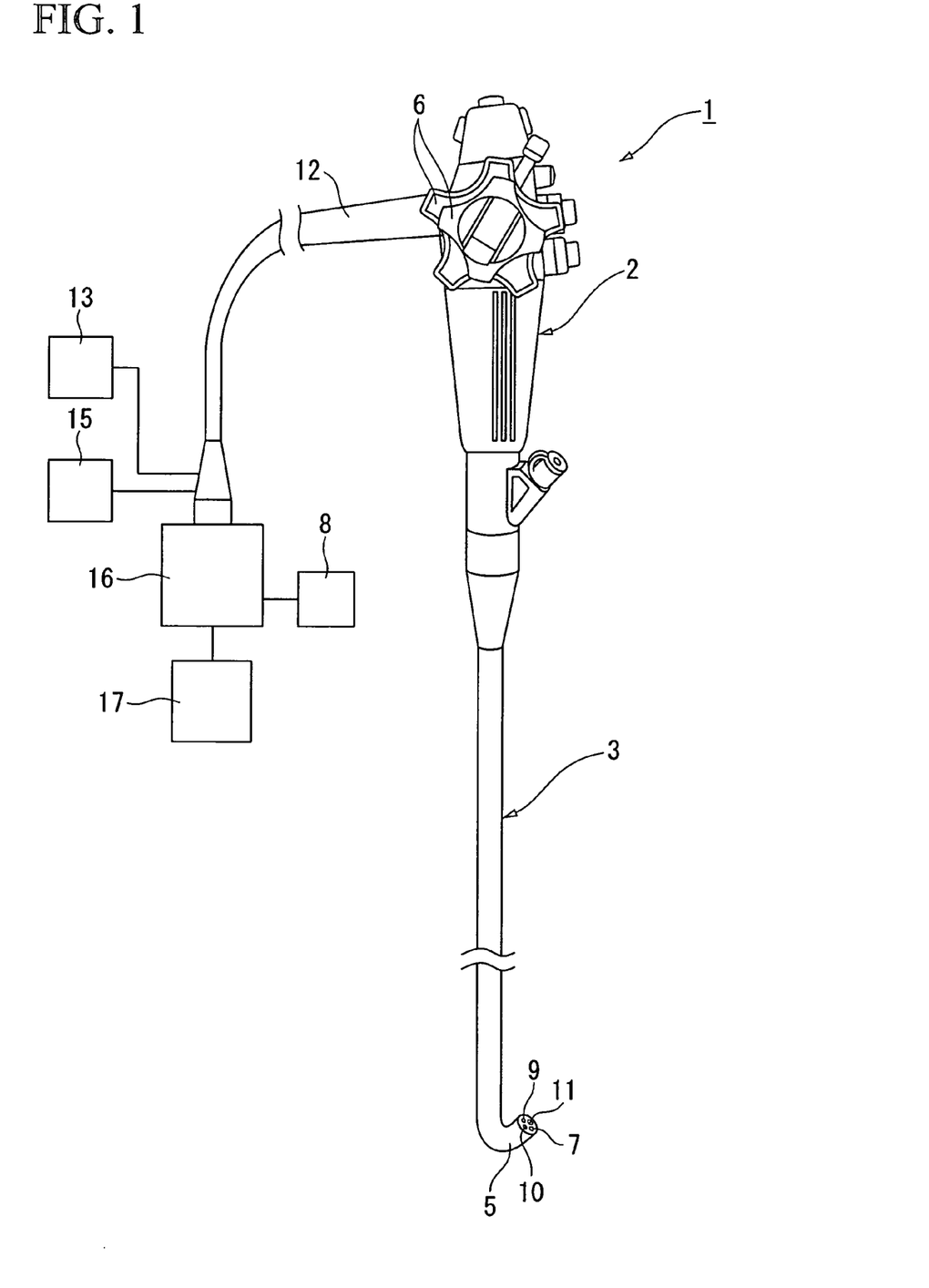
FIG. 1 is a view showing an endoscope employed in the first embodiment, as one example of a device used in a medical procedure.

A flexible endoscope (referred to as "endoscope" hereinafter) 1 is shown in FIG. 1 as an example of a device employed in the present embodiment. The endoscope 1 is provided with an elongated insertion part 3 that extends out from an operation part 2, which is manipulated by the operator. An insertion part 3 has flexibility, and is inserted into the patient's body. The end 5 of the insertion part 3 can be bent by operating an angle knob 6 that is disposed to the operation part 2. An observation device (alternatively referred to as "observation device") 7, composed of an optical system for observation such as an objective lens or the like, and a CCD, used as an image pick-up element; an illuminating device 9 composed of an optical fiber for guiding light from a light source device 8 disposed outside the body, and an illuminating optical member for forming the light rays radiated from the end surface of the optical fiber into a desired form; and the end openings for channels 10 and 11; are disposed to the end of the insertion part 3. The channel 10 is a conduit that is connected to a gas/water supplying device 13 that is disposed outside the body, via a universal cable 12, and that is employed for supplying and evacuating liquid to and from the body. The channel 11 is a conduit that is attached to a suction device 15 or that is employed for inserting and removing instruments. The observed image that is input to the observation device 7 is displayed on a monitor 17 via a controller 16.

Figure 2:
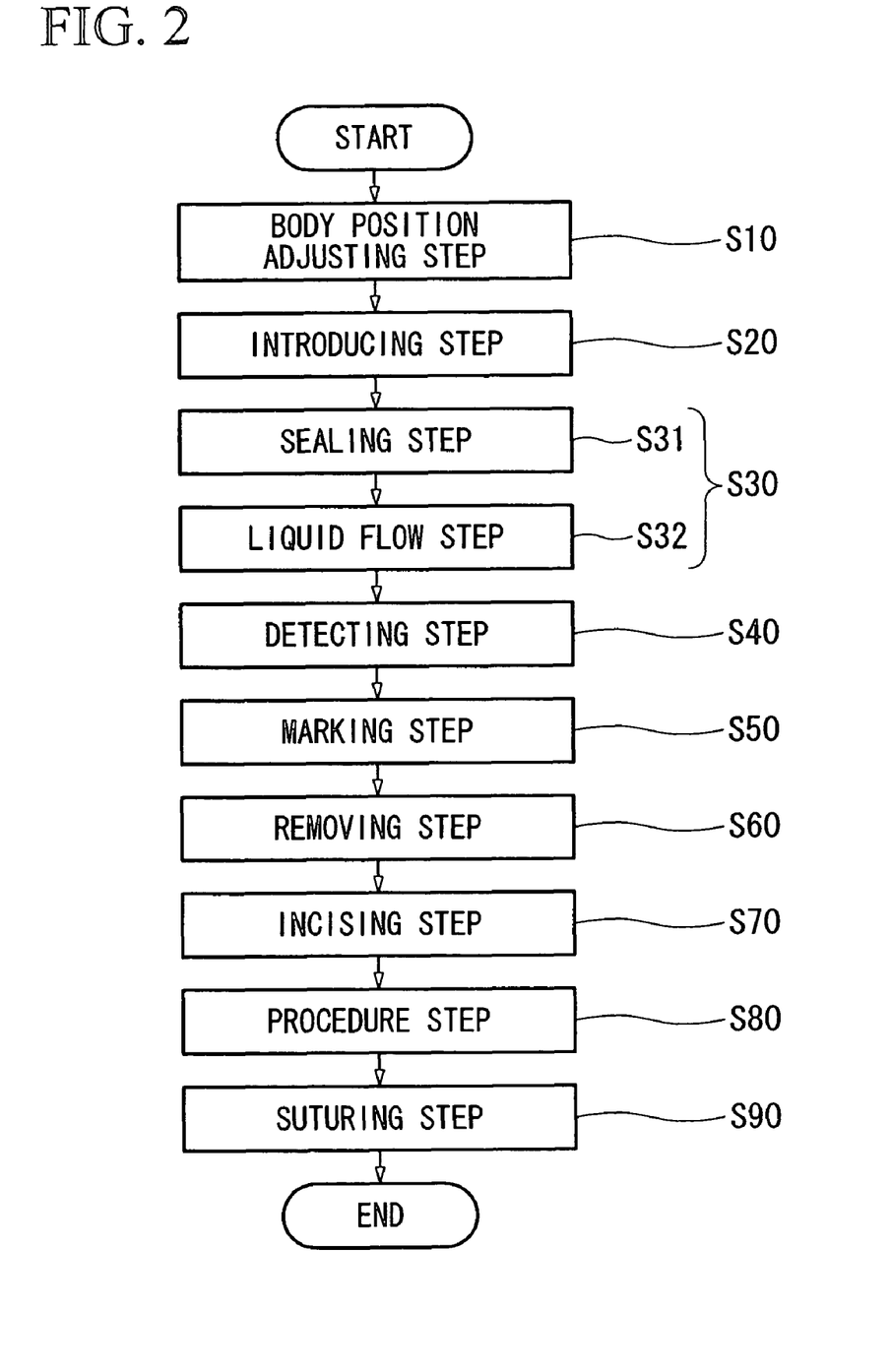
FIG. 2 is a flow diagram showing a medical procedure according to the first embodiment.

The effects of the present embodiment in which this endoscope 1 is employed will be explained following the flow diagram shown in FIG. 2. Note that the following discussion explains a procedure in which the endoscope 1, which is an example of a procedure device for performing a specific procedure, is inserted via the mouth M of a patient PT into the stomach (hollow organ) ST, an opening is formed in the stomach wall, the insertion part 3 of the endoscope 1 is inserted into the abdominal cavity AC, and a procedure is performed. Note that in this case, the natural orifice into which the endoscope 1 is inserted is not limited to the mouth M; rather, this explanation is applicable to the nostrils, anus, or any other natural opening. With regard to the medical procedure carried out in the abdominal cavity AC, a variety of procedures, such as suturing, observation, incising, resection, cellular sampling, removal of a body organ or the like, may be carried out alone or in combination.

First, in body position adjusting step (S10), the body position of the patient PT is adjusted so that a target site T on the anterior wall of the stomach ST faces in the direction opposite the direction of gravitational force. In this embodiment, an arrangement is employed in which the patient PT is placed on his/her back, so that the anterior wall of the stomach ST, where the target site T is located, is directed upward.

Figure 3:
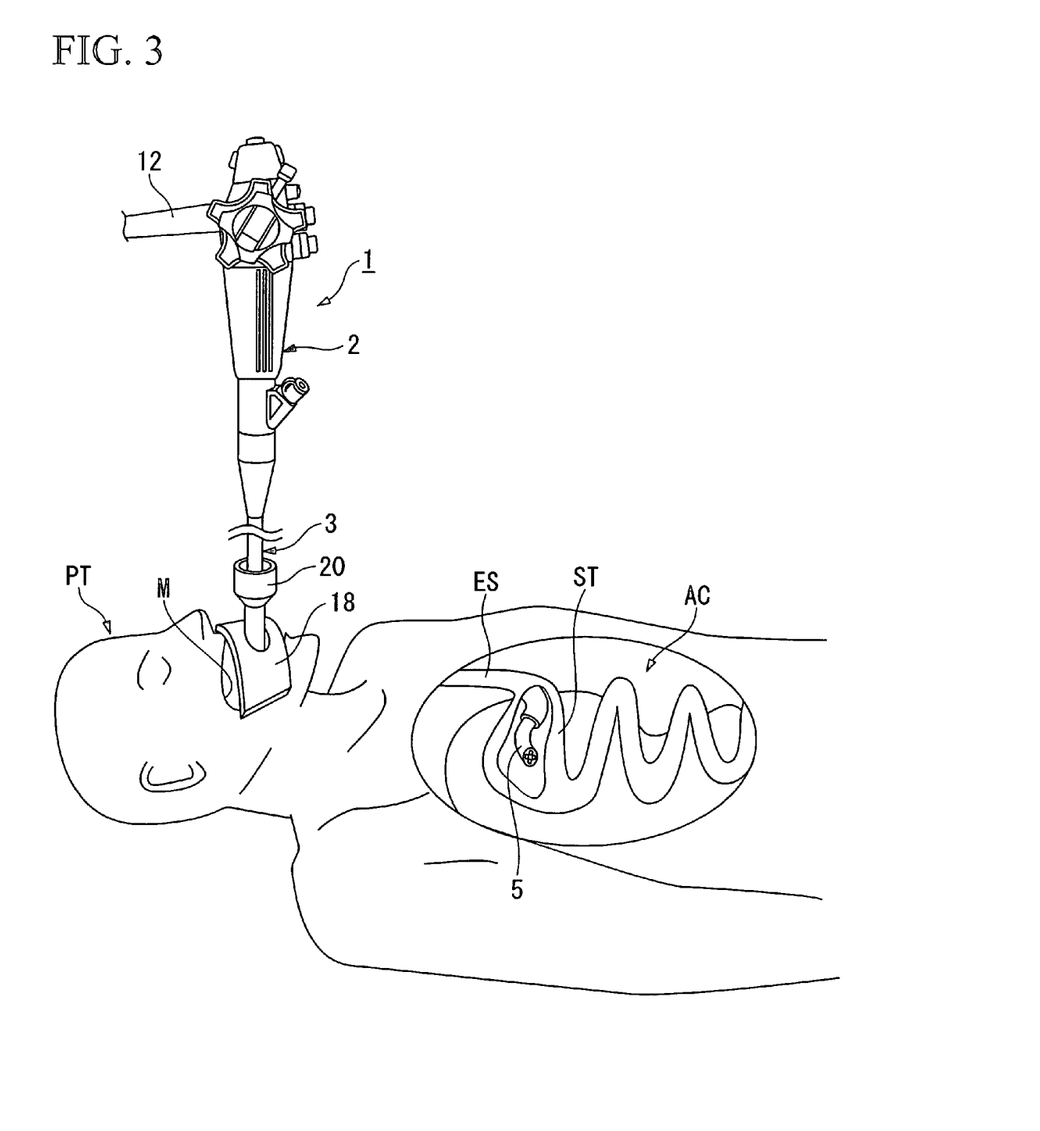
FIG. 3 is a view for explaining the arrangement for inserting the endoscope into the stomach, in a procedure according to the first embodiment.

Next, guiding step (S20), in which the endoscope 1 is inserted into the stomach ST, is carried out. Namely, a mouth piece 18 is attached at the mouth of the patient PT, and the endoscope 1 is inserted into the esophagus ES. It is preferable here to incorporate an overtube 20 during insertion of the endoscope into the body, as shown in FIG. 3. The overtube 20 is employed as a guide tube for inserting the endoscope 1 or another such device having an insertion part. However, it is also acceptable to directly insert the endoscope 1 without employing the overtube 20.

In the case where inserting the endoscope using the overtube 20, an attaching balloon (sealing member) 21 is attached at the distal end of the overtube 20. As shown in FIG. 3, the overtube 20 and the end of the insertion part 3 of the endoscope 1 are inserted into the stomach ST.

Next, the process proceeds to the area forming step (S30). A sealing step (S31) is first carried out in which the outlet side of the stomach ST (i.e., the forward direction of insertion of the endoscope) near the target site T (anterior wall of the stomach in this embodiment) is sealed. Specifically, an instrument is inserted into channel 11 of the endoscope 1, and a retaining balloon (sealing member) 22 is disposed in the duodenum Du in the forward direction of insertion of the endoscope 1. This retaining balloon 22 is then inflated in this position. The instrument is then removed, so that the retaining balloon 22 remains and seals the pylorus PS of the stomach ST. Sealing of the inlet side (i.e., the cardia CS side) of the stomach ST is then performed. Specifically, the attaching balloon 21 provided to the overtube 20 is inflated, sealing the space between the overtube 20 and the cardia CS. The space formed between the inner surface of the overtube 20 and the surface of a device such as the endoscope 1 that is inserted therein is sealed with a sealing member such as a valve, not shown in the figures, that is provided to the overtube 20. Note that, in this embodiment, both sides of the stomach ST (i.e., the one side and the other side of the hollow organ that have the area of the target site disposed therebetween) are sealed using sealing members such as attaching balloon 21 and the retaining balloon 22. However, it is also acceptable to omit sealing of the inlet side (i.e., the side into which the endoscope 1 or the overtube 20 is inserted) of the stomach ST. This is because in the case of the inlet side of the stomach ST, seal-tightness of the hollow organ can be assured to a certain degree by means of the inserted device such as the endoscope 1 or the overtube 20, as compared to the outlet side (i.e., the cardia CS side or the forward direction of insertion of the endoscope 1) of the stomach ST.

Figure 4:
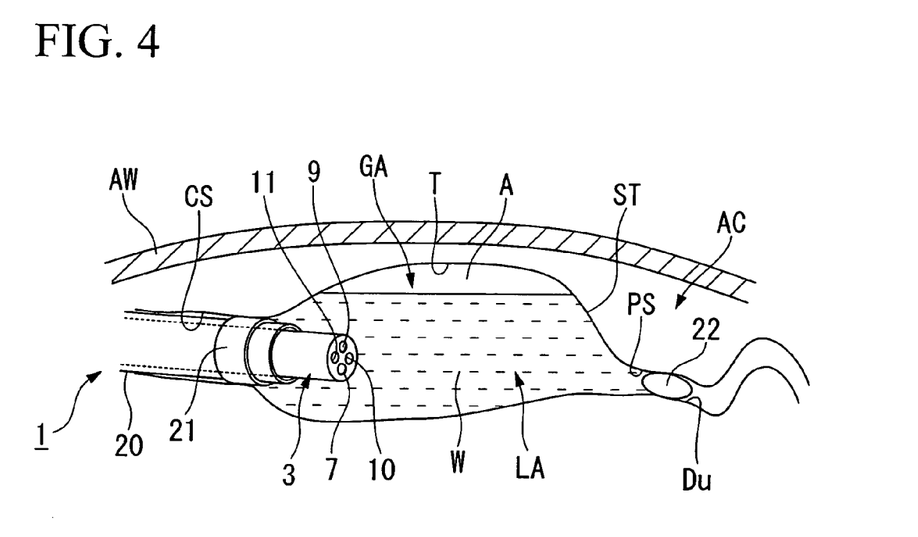
FIG. 4 is a view for explaining the arrangement for sending water by inserting an endoscope into the stomach, in a procedure according to the first embodiment.

Next, the process proceeds to the liquid inflow step (S32). In this step, water is supplied into the stomach ST from channel 11 of the endoscope 1 which has been introduced into the stomach ST. Since both the cardia CS and the pylorus PS of the stomach ST are sealed at this time, water is held in the stomach ST as shown in FIG. 4. Since water W is heavier than air A, the water W supplied into the stomach ST is held in the bottom portion of the stomach ST, while air A rises to the top of the stomach ST. The target site T is positioned at the top of the stomach ST, where it is not exposed to water. In this way, a lower liquid holding area LA, and an upper gas retaining area GA, where gas remains and where the target site T is located, are formed.

Figure 5:
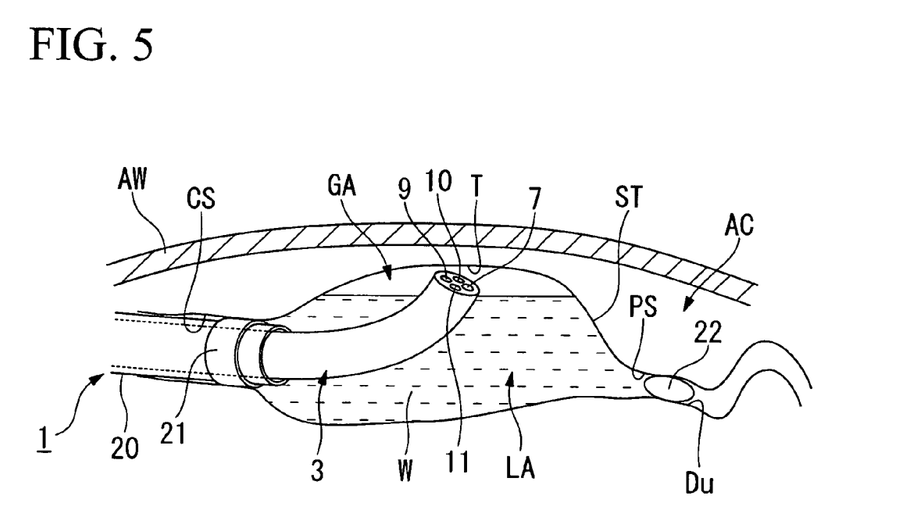
FIG. 5 is a view for explaining the arrangement in which the insertion part of the endoscope has been directed to the gas retaining area, in a procedure according to the first embodiment.

The process then proceeds on to detecting step (S40). In this step, the angle knob 6 is operated to bend and manipulate the end of the insertion part 3 inside the stomach ST. The position of gas retaining area GA is confirmed during this operation, and the end of the insertion part 3 is moved from liquid holding area LA to gas retaining area GA. In this way, target incision site T is confirmed using the observation device 7, as shown in FIG. 5.

Figure 6:
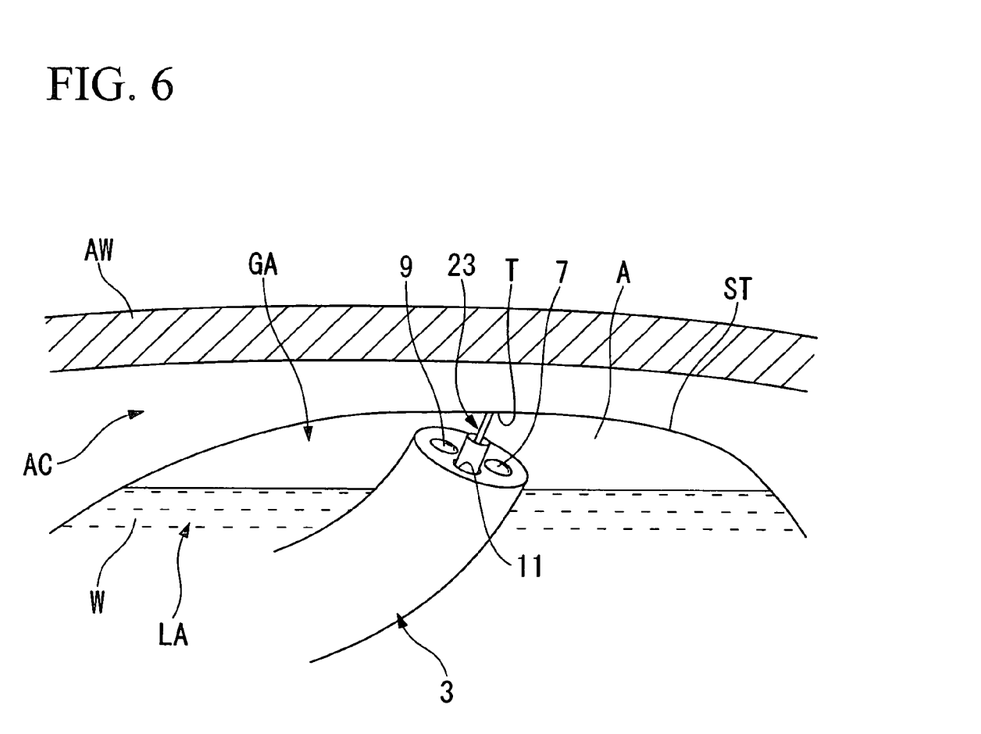
FIG. 6 is a view for explaining the arrangement for marking the target site, in a procedure according to the first embodiment.

Next, in marking step (S50), a the marking instrument 23 such as a high frequency knife, used for marking the stomach wall, is inserted into the channel 11 of the insertion part 3, and marking near the target site T is carried out as shown in FIG. 6. In order to prevent a short circuit, note that it is first confirmed that the area around the marking site is completely within gas retaining area GA. It is also acceptable to carry out this marking using a retained member, such as a clip or the like.

Once marking is completed, removing step (S60) is carried out. Namely, the marking instrument 23 is withdrawn from the channel 11, and the channel 11 and the suction device 13 are connected. The suction device 15 is then activated to remove the water W remaining in the stomach ST, expelling it to the outside of the body via the channel 11 of the endoscope 1.

Figure 7:
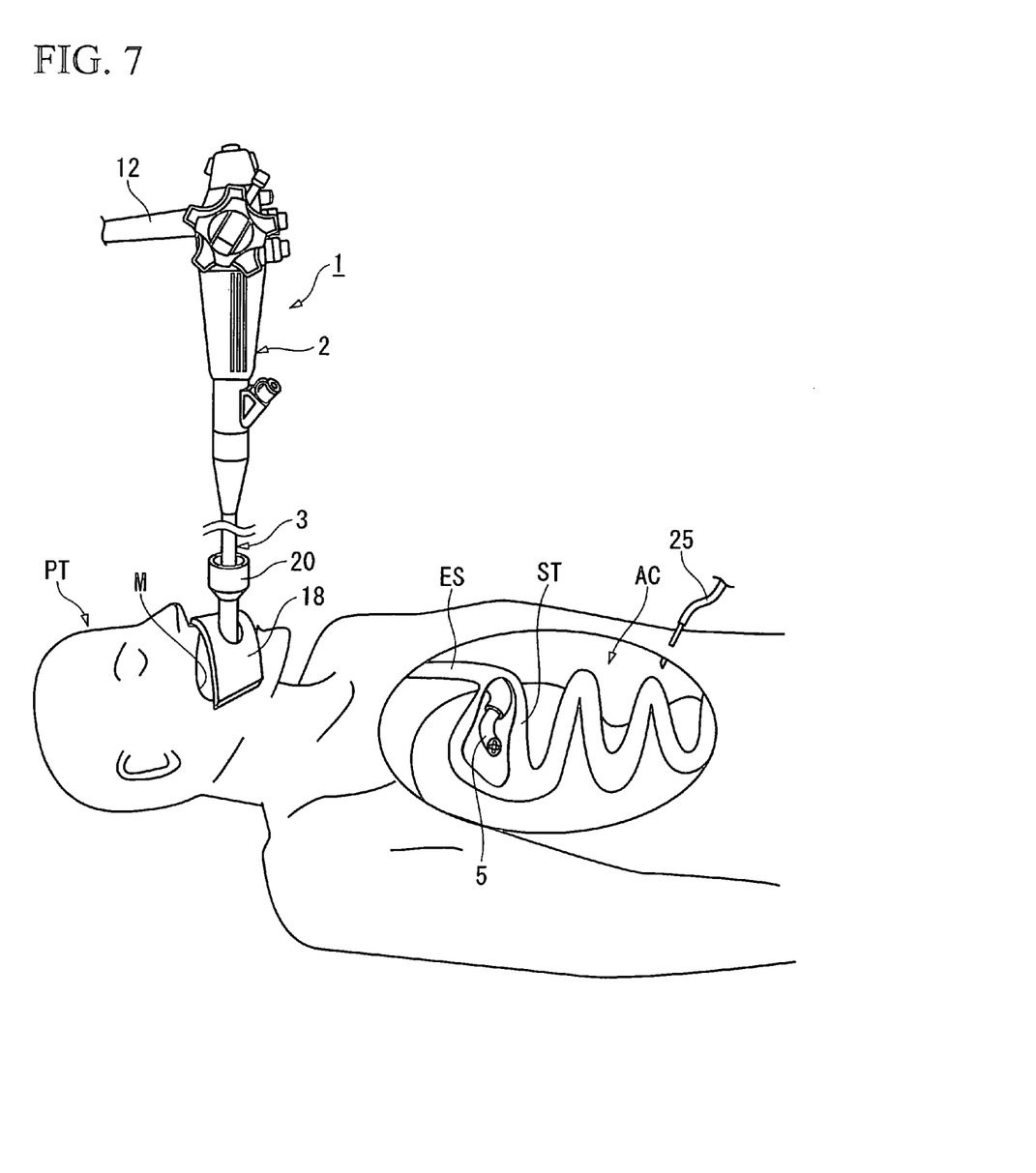
FIG. 7 is a view for explaining the arrangement for an insufflation, in a procedure according to the first embodiment.

The process then proceeds to incising step (S70). The end of an insufflation needle (a conduit for supplying gas) 25 is passed from outside the body through an abdominal wall AW, and into the abdominal cavity AC, as shown in FIG. 7, for example. The abdominal cavity AC is then inflated with gas via the insufflation needle 25, to create a space between the stomach wall and the abdominal wall AW. In this embodiment, space between the stomach wall and the abdominal wall AW is secured by insufflating the abdominal cavity AC; however, it is not absolutely essential to carry out an insufflation step. Namely, it is also acceptable to employ conventionally known methods such as the suspension method to provide this space. In addition, it is also acceptable to perform the insufflating step in advance of the incising step. In addition, insufflation of the hollow organ is not absolutely required.

Next, the marking instrument 23 disposed inside the channel 11 is removed, and a high frequency knife for cutting is passed in its place through the channel 11 to extend out from the end opening. The marked target site T is then incised while observation the target site T on the monitor 17, to form an opening SO in the stomach wall (at a position corresponding to the target site T), the opening SO creating a communication between the inside of the stomach ST and the abdominal cavity AC. Note that a combined use instrument may be employed for the marking instrument and the instrument for forming the opening SO.

Figure 8:
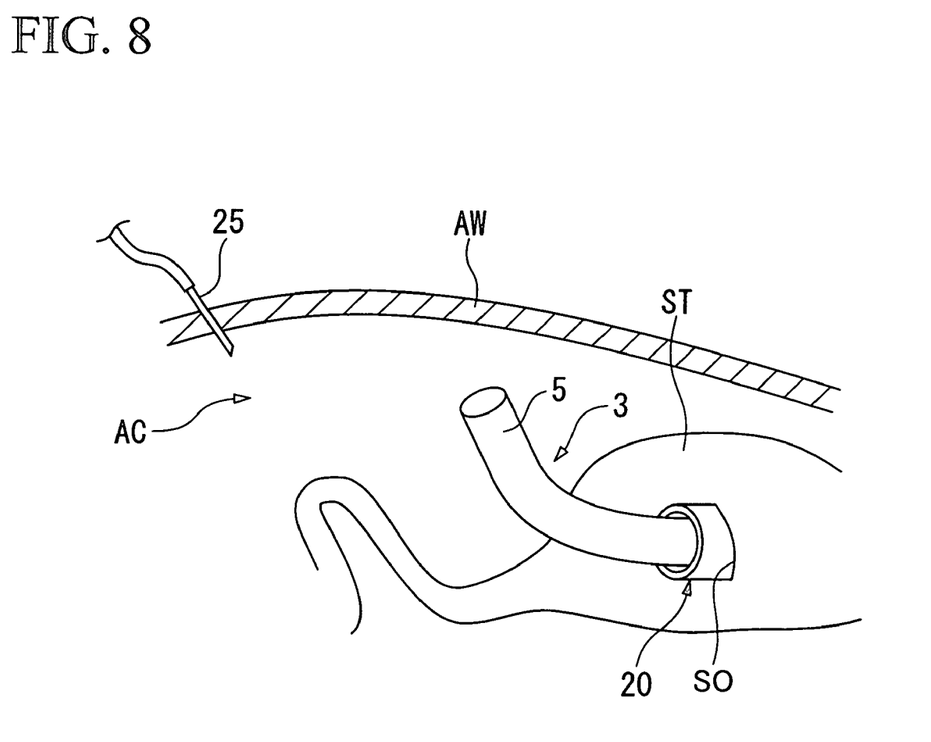
FIG. 8 is a view for explaining the state in which an opening has been incised in the stomach, in a procedure according to the first embodiment.

After incising, as shown in FIG. 8, the end of the insertion part 3 is projected out into the abdominal cavity AC through the opening SO in the stomach wall, and procedure step (S80) is carried out in which various procedures such as suturing, observation, incising, resection, cell collection, organ removal or the like, are performed.

Next, the process proceeds to suturing step (S90), in which the opening SO in the stomach wall is sutured closed (the communicating path between the inside of the hollow organ and the abdominal cavity is closed) with a suturing instrument while using the observation device 7 of the endoscope 1 for confirmation.

After suturing, the endoscope 1 is withdrawn from the patient. In the case where the medical procedure was performed by blowing carbon dioxide gas or the like into the abdominal cavity AC in order to secure space within the abdominal cavity, it is desirable to withdraw the insufflation needle 25 after first relieving the pressure within the abdominal cavity AC, and then conclude the medical procedure.

In this embodiment, water was supplied into the stomach ST after positioning the patient PT so that the target site T is on top. As a result, by searching for the gas retaining area (GA) inside the stomach ST, it is possible to confirm the up/down direction from inside the stomach ST, and the target site T can be gripped. The stomach ST is sealed using attaching balloon 21 and the retaining balloon 22 during this operation. As a result, it is possible to grip the target site T by sending and expelling water to and from the stomach ST using the devices of a conventional endoscope 1, without requiring use of special equipment.

Since an incision is made in the anterior wall of the stomach ST, it is easy to avoid the greater omentum or other organs when introducing the endoscope into the abdominal cavity AC. As a result, the endoscope 1 can be readily inserted into the abdominal cavity AC, further facilitating the procedure.

In the past, it has been difficult to specify the direction or the location for a procedure (i.e. the location suitable for forming an opening) by means of the endoscope image alone, and practice was required for this procedure. However, in this embodiment, confirmation of the site is facilitated, reducing the burden on the operator.

In the first embodiment described above, the channel 10 is employed as a conduit for supplying water, and the channel 11 has a combined use as a conduit for inserting and passing instruments and as a conduit for expelling water. As another example, however, it is also acceptable to provide a combined use water supplying conduit and instrument inserting and passing conduit. In addition, a design is also acceptable in which the three functions of supplying water, expelling water, and instrument inserting/passing are accomplished by means of a single conduit. In addition, the hollow organ anterior and posterior to the target site were sealed using a sealing member, however, when it is possible to determine the direction of gravitational force and the direction opposite that using just a small amount of water, then it is not absolutely essential to carry out the sealing step.

Second Embodiment

A second embodiment will now be explained with reference to the figures.

The difference between the second and first embodiments is that, in this embodiment, the stomach ST is inflated with water, after which air is introduced into the stomach ST, and the target site T is searched for using the direction of movement of the air bubbles.

Figure 9:
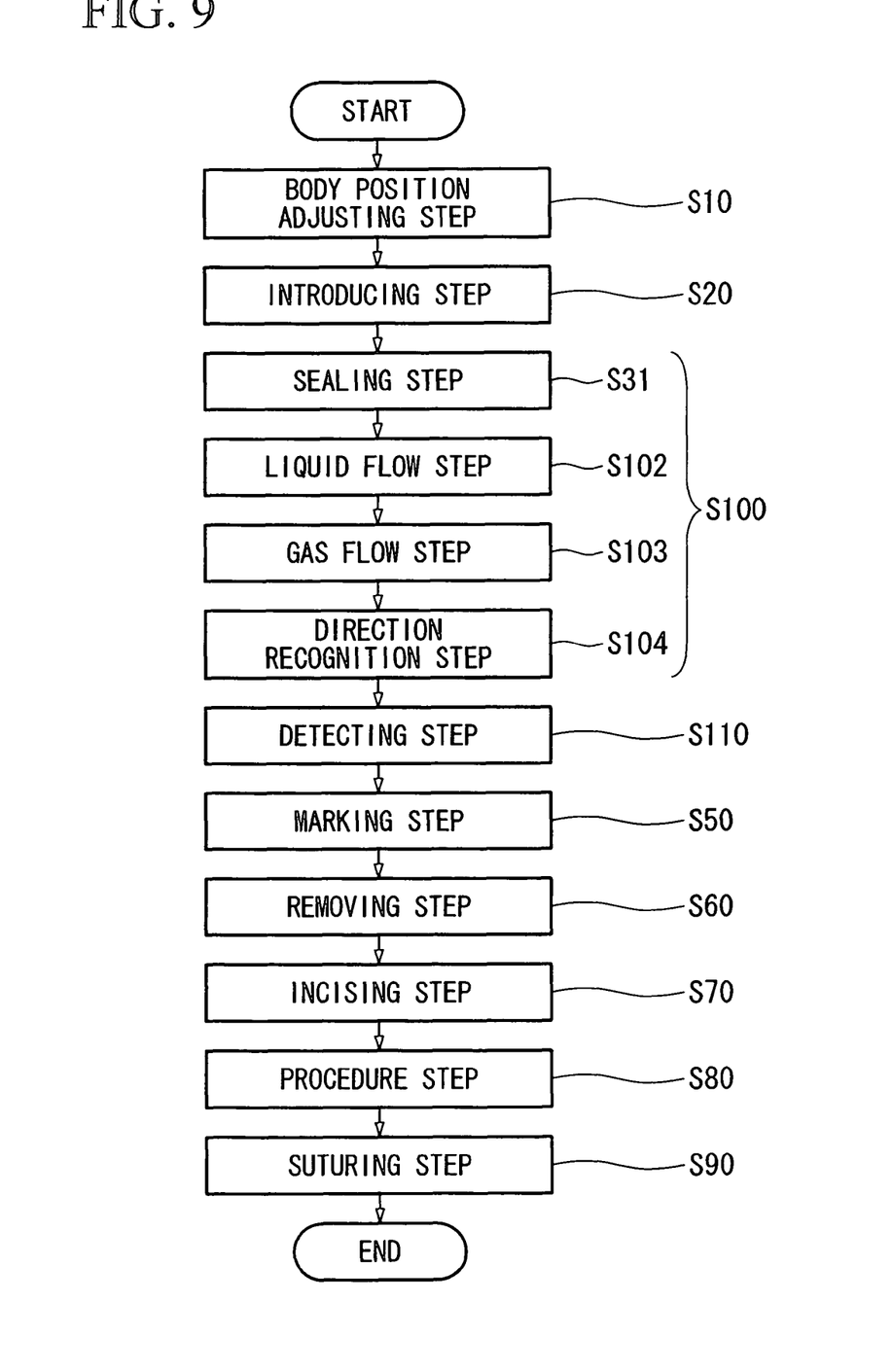
FIG. 9 is a flow diagram showing a medical procedure according to the second embodiment.

The effects of this embodiment will be explained following the flow shown in FIG. 9

First, the body position adjusting step (S10) and introducing step (S20) are carried out in the same manner as in the first embodiment. Namely, the position of the patient PT is adjusted so that the target site T is directed upward, and the overtube 20 and the endoscope 1 are inserted into the stomach ST.

Next, the process proceeds to area forming step (S100). First, sealing step (S31) is carried out, in which the retaining balloon 22 is retained in duodenum Du. In this way, the pylorus PS of the stomach ST and the cardia CS of the stomach ST are sealed.

Figure 10:
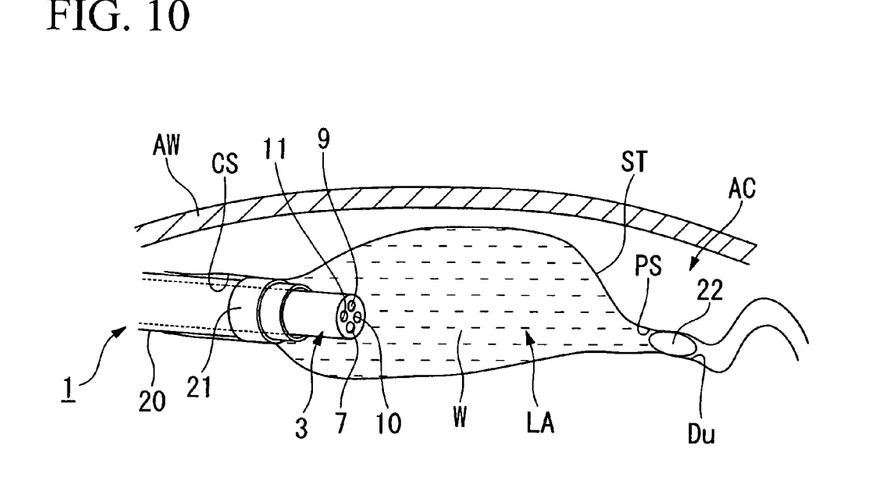
FIG. 10 is a view for explaining the arrangement in which water is supplied into the stomach to inflate it, in a procedure according to the second embodiment.
Figure 11:
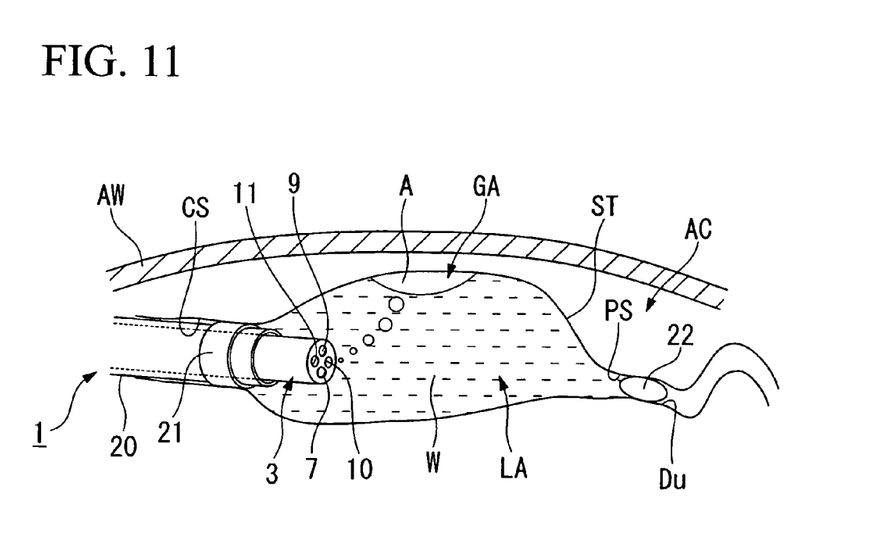
FIG. 11 is a view for explaining the arrangement for confirming the direction of movement of bubbles using the insertion part of the endoscope, in a procedure according to the second embodiment.

Next, the process proceeds to liquid inflow step (S102). As shown in FIG. 10, water is supplied into the stomach ST via the channel 11 of the endoscope 1 which has been inserted into the stomach ST, inflating the stomach ST with water W. Once the stomach ST is inflated, the process proceeds to gas inflow step (S103). Namely, air A is introduced into the stomach ST from an air/water supplying device 13 via the channel 10 of the endoscope 1. Since air A is lighter than water W, the air A introduced into the stomach ST forms bubbles B and moves through water W to the top of the stomach ST, as shown in FIG. 11. In this way, a liquid holding area LA is formed at the bottom and a gas retaining area GA, where the air remains, is formed at the top within the stomach ST.

Direction recognition step (S104) is executed almost simultaneously. Namely, the movement behavior of bubbles B from air A expelled from the end of the insertion part 3 of the endoscope 1 in gas inflow step (S103) is observed, thereby allowing determination of the up/down direction within the stomach ST (alternatively, the up/down direction in the stomach ST may be determined by determining the direction where gas retaining area GA is formed).

Next, the process proceeds to detecting step (S110). The end of the insertion part 3 is moved from liquid holding area LA to gas retaining area GA while being bent and manipulated by operating the angle knob 6.

Subsequently, the marking step (S50), removing step (S60), incising step (S70), procedure step (S80), and suturing step (S90) are each executed in the same manner as in the first embodiment. After suturing is completed, the endoscope 1 is removed from the patient, the insufflation needle 25 is removed after relieving the pressure inside the abdominal cavity AC, and the procedure is terminated.

In this embodiment, the up/down direction in the stomach ST was determined by observing bubbles B moving through water W. As a result, gas-retaining area GA can be recognized more easily than in the first embodiment, and searching for the target site T is facilitated. Note that in the second embodiment, the channel 11 is used as a water supplying conduit and the channel 10 is used as a gas supplying conduit. However, as a separate example, a design is also acceptable in which the water supplying conduit and the gas supplying conduit are accomplished as single conduits. Alternatively, it is also acceptable to provide a combined use water supplying conduit and gas supplying conduit. In addition, a design may also be employed in which all the functions are carried out through a single conduit.

The technical scope of the present invention is not limited to the embodiments described above. Rather, various modifications may be added provided that they do not depart from the spirit of the invention.

For example, the stomach was employed as an example of a hollow organ in the above embodiments. However, the present invention is not limited thereto; rather, the present invention may be used with other hollow organs into which an endoscope can be inserted via a natural opening. In addition, while water was supplied into the stomach ST in the above embodiments, it is also acceptable to supply a liquid medication. When a antibacterial agent is used as the medication, then it is possible to carry out the procedure in combination with disinfecting the stomach to remove such bacteria as *pylori* sp. It is also acceptable to use an antibiotic as the liquid medication. Further, the sequence for the various steps of the medical procedure is not limited to that disclosed in the preceding embodiments; any sequence is permissible, provided that it allows liquid to be supplied into the hollow organ. The same procedure may also be carried out while observation the inside of the body using an observation device of the type that wirelessly sends images taken up by a conventionally known capsule endoscope or other such equipment that is retained inside the body, or a wireless type observation device that uses a device (i.e., device for performing a procedure) having an insertion part that does not have a observation function.

The above embodiments showed a medical procedure using an overtube, however, it is also acceptable to insert the endoscope into the body without using the overtube. In this case, it is possible to provide an attaching balloon identical to that of the embodiments, to the insertion part of the endoscope, to seal the space between the insertion part and the hollow organ.

What is claimed is:

1. A medical procedure for detecting a target site for forming an opening which communicates between an abdominal cavity and a hollow organ using an image of the site which is captured by an observation device inserted into a body via a natural opening, the medical procedure comprising the successive steps of:
    adjusting a position of a patient's body so that an anterior wall containing the target site of an inner cavity faces opposite to a direction of gravitational force;
    introducing the observation device into the patient's body;
    flowing liquid into the inner cavity so as to form a gas retaining area consisting of gas remaining in the inner cavity and a liquid holding area consisting of the introduced liquid held in the inner cavity;
    detecting the target site for forming the opening which communicates between the abdominal cavity and the hollow organ on an anterior wall of the inner cavity which is in contact with the gas retaining area based on a positional relationship between the gas retaining area and the liquid holding area, in which an image of the positional relationship is captured and displayed on a screen of the observation device when the position of the patient's body is in the position; and
    forming the opening which communicates between the abdominal cavity and the hollow organ.

2. The medical procedure via a natural opening according to claim 1, further comprising introducing said observation device and a liquid inflow conduit into a hollow organ via a natural opening.

3. The medical procedure via a natural opening according to claim 2, wherein said hollow organ in the vicinity of said target site is sealed in at least the direction of insertion of the liquid inflow conduit into the patient.

4. The medical procedure via a natural opening according to claim 2, wherein:
    forming said gas retaining area comprises introducing a conduit for supplying gas into said liquid holding area and introducing gas via said gas supplying conduit, and
    observing the gas retaining area by the observation device comprises confirming the direction of movement of bubbles formed from air that was supplied from said gas conduit into said liquid holding area.

5. The medical procedure via a natural opening according to claim 2, further comprising:
    performing marking to the anterior wall of said hollow organ in said gas retaining area, using an instrument introduced via a natural opening; and
    removing said liquid from said hollow organ via said liquid inflow conduit.

6. The medical procedure via a natural opening according to claim 2, further comprising:
    disposing balloons that can expand and contract to said hollow organ on either side of said target site, for controlling the fluid outflow from said target site.

7. The medical procedure via a natural opening according to claim 2, wherein:
    introducing said observation device and said liquid inflow conduit into said hollow organ comprises introducing into said hollow organ an endoscope in which said observation device and said liquid inflow conduit are disposed to the insertion part of the endoscope that is introduced into the body.

8. The medical procedure via a natural opening according to claim 4, wherein introducing said observation device, said liquid inflow conduit, and said gas supplying conduit into said hollow organ comprises introducing into said hollow organ an endoscope in which said observation device, said liquid inflow conduit and said gas supplying conduit are disposed to the insertion part of the endoscope.

9. The medical procedure via a natural opening according to claim 2, further comprising:
    incising the anterior wall of the stomach to form an opening.

10. The medical procedure via a natural opening according to claim 9, further comprising introducing a procedure device into the abdominal cavity by passing through said opening, and performing a specific procedure inside said abdominal cavity.

11. The medical procedure via a natural opening according to claim 1, further comprising:
    inserting a procedure device into the abdominal cavity via said opening, and performing a specific procedure inside said abdominal cavity using said device;
    withdrawing said device into said hollow organ after said specific procedure has been carried out inside said abdominal cavity; and
    closing the communicating path between said hollow organ and said abdominal cavity that passes through said opening.

12. The medical procedure via a natural opening according to claim 1, further comprising:
    introducing the observation device into the liquid holding area formed inside of the hollow organ, and
    moving an optical system for observation of the observation device from the liquid holding area into the gas retaining area so as to confirm the target site based on the position of the gas retaining area.

13. The medical procedure via a natural opening according to claim 1, wherein the target site on the anterior wall of the hollow organ captured on the screen of the observation device is detected based on a direction of movement of bubbles formed from air supplied from the gas conduit into the liquid holding area.

* * * * *